(12) United States Patent
Velez-Cruz

(10) Patent No.: US 10,492,827 B1
(45) Date of Patent: Dec. 3, 2019

(54) DEVICE FOR ORTHOPEDIC AND GENERAL SURGERIES

(71) Applicant: Alex Joel Velez-Cruz, Bayamon, PR (US)

(72) Inventor: Alex Joel Velez-Cruz, Bayamon, PR (US)

( * ) Notice: Subject to any disclaimer, the term of this patent is extended or adjusted under 35 U.S.C. 154(b) by 0 days.

(21) Appl. No.: 16/526,798

(22) Filed: Jul. 30, 2019

Related U.S. Application Data

(60) Provisional application No. 62/716,006, filed on Aug. 8, 2018.

(51) Int. Cl.
*A61B 1/32* (2006.01)
*A61B 17/34* (2006.01)
*A61B 1/313* (2006.01)
*A61M 39/02* (2006.01)

(52) U.S. Cl.
CPC ...... *A61B 17/3421* (2013.01); *A61B 17/3462* (2013.01); *A61B 1/3132* (2013.01); *A61B 2017/3445* (2013.01); *A61B 2217/005* (2013.01); *A61B 2217/007* (2013.01); *A61M 39/0247* (2013.01)

(58) Field of Classification Search
CPC combination set(s) only.
See application file for complete search history.

(56) References Cited

U.S. PATENT DOCUMENTS

2006/0293560 A1* 12/2006 Nguyen ............... A61B 17/42
600/104

* cited by examiner

*Primary Examiner* — Sameh R Boles
(74) *Attorney, Agent, or Firm* — University of Puerto Rico; Eugenio J. Torres-Oyola; Victor M. Rodriguez-Reyes

(57) ABSTRACT

The invention relates to a surgical cannula for introducing instruments, scopes or tubing into body cavities while saline water can be provided or waste material can be removed at the same time. and within the same incision. The cannula has a tee shape with two ports on sides and is capable to combines the uses of supply saline water, remove damaged material and perform manipulation of surgical instruments within an incision. The cannula invention reduced at least one incision and saved time during surgical procedures.

7 Claims, 5 Drawing Sheets

DEVICE FOR ORTHOPEDIC AND GENERAL SURGERIES

BACKGROUND OF THE INVENTION

The present invention is in the technical field of medical devices. The cannulas are medical devices used by orthopedic and general surgeons with the intent to allow them to visualize instrumentation passing through the skin and layers of the body and also to maintain an open area to add saline water during the surgery process and remove damage material from the interior of the body.

Typically, orthopedic and general surgeons choose arthroscopic surgeries over traditional open surgery due to the fact that the joint does not have to be opened up fully. This technique is considered as a minimally invasive surgical procedure. Currently, arthroscopic surgeries are performed using three or four small incisions of 1 cm long approximately. The first incision is dedicated for use of the arthroscope device (tiny camera), second and third for the use of several surgical instruments (if the third is needed) and fourth for the supply of saline solution and removal of waste material in the joint cavity. This procedure reduces recovery time and may increase the rate of success due to less trauma to the connective tissue. There is also less scarring, because of the smaller incisions.

Much of the focus in recent years has centered on less invasive procedures. Such well-established and successful interventions as total hip replacement, rotator cuff surgery, total knee replacement, shoulder stabilization surgery, gall bladder removal, uterus and colon repairs and others are being done through surgical approaches that minimize skin incisions. The advocates of these procedures cite decreased recuperation time, decreased morbidity, decreased pain, and fewer days of hospitalization as advantages of these procedures.

SUMMARY OF THE INVENTION

This invention provides a translucent or transparent plastic cannula with the capability to support the use of surgical instrumentation passing through. The cannula device is intended to provide saline water and remove damaged material from the interior of the affected area while the surgeon uses other surgical instruments through the same passage. The cannula device has a dedicated saline water supply and vacuum ports for the use of a surgeon as needed. The cannula prevents the "fall out" effect while the surgery is performed. The cannula withstands the impact force or the breaking point material if for some reason encountering a bone or other hard object.

The new biomedical device is meant to reduce at least one incision in the arthroscopic, laparoscopic and general surgical procedures and minimize the time of the procedures as well. The cannula device can be re-used for laparoscopic or general surgeries, but it may also be disposable for orthopedic applications. This new cannula will prevent additional incisions caused due to the use of supply saline solution and removal of waste material. The cannula has the capability to combine the functions of the supply and suction ports with the passage used by surgeons to introduce their surgical instruments. Also, if surgeons do not use a portal passage (cannula) for adequate management of the surgical instruments, the skin impacted will be affected, so it is highly recommended to place the cannulas properly to allow access of the surgical instruments. This will minimize the interaction between surgical instruments and skin, which could result in future trauma for constant removal of surgical instruments.

DETAILED DESCRIPTION OF THE INVENTION

Figure 1:
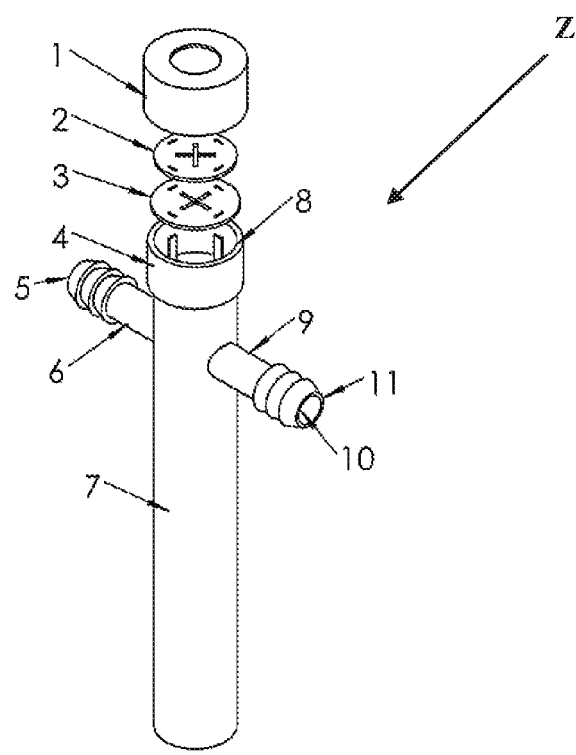
FIG. 1 is an isometric view of the present invention.

FIG. 1 shows a cannula device Z having a main body 7, which may be cylindrical in shape, that comprises a top open end, a bottom open end and a hollow interior or inner portion that is capable of receiving fluids. The cannula device Z further comprises a cap seal 1 that is removably attached to the top open end of the cannula device Z; a top membrane 2 which prevents the backflow of water; a bottom membrane 3 which prevents backflow of water; and a membrane base 4 located at the top end, that provides structural support to the top membrane 2 and bottom 3 membrane. The cannula device Z also comprises a water supply port 5 whose external or outer diameter is in contact with the environment; a water supply tube 6 which is an inlet port for receiving saline water and is transversally connected to the main body 7; a cannula cap 8 surrounding the top open end of the main body 7 that is thicker than the main body 7, thus providing structural support to the cap seal 1; a suction port tube 9 which is an outlet port for removing waste material that is transversally connected to the main body 7; said suction port tube 9 comprises an inner diameter 10 that is in contact with waste material and an outer diameter 11 that is in contact with the environment. In addition, the outer portion of the main body 7 further comprises a cannula sleeve or outer portion that is in contact with the environment.

Figure 2:
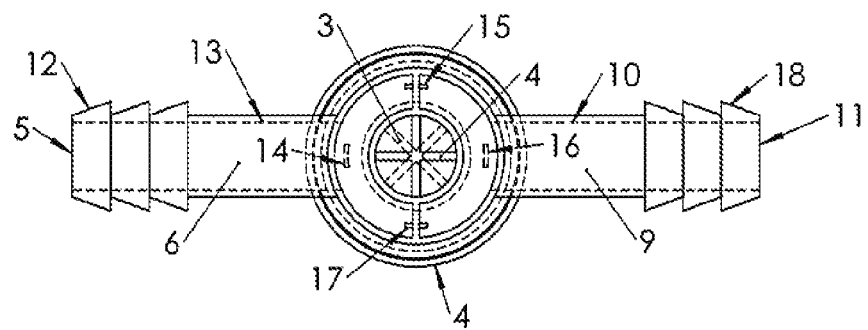
FIG. 2 is a top view of the present invention.

FIG. 2 shows the bottom membrane 3 of the cannula device Z which prevents backflow of water; the membrane base 4 which provides structural support to the top membrane 2 and bottom membrane 3; the water supply port outer diameter 5 which is the external diameter in contact with the environment; the water supply tube 6 which is an inlet port to provide saline water; the suction port tube 9 which is an outlet port to remove waste material; the suction port inner diameter 10 which is the internal diameter in contact with waste material; the suction port outer diameter 11 which is the external diameter in contact with the environment; a water supply port total outer grip 12 which is an external threaded surface; a water supply port inner diameter 13 which its internal diameters in contact with fluids; a membrane holder 14 which provides support to top and bottom membranes; a membrane holder 15 which provides support to top and bottom membranes; a membrane holder 16 which provides support to top and bottom membranes; a membrane holder 17 which provides support to top and bottom membranes; and a suction port total outer diameter grip 18 which is an external threaded surface.

Figure 3:
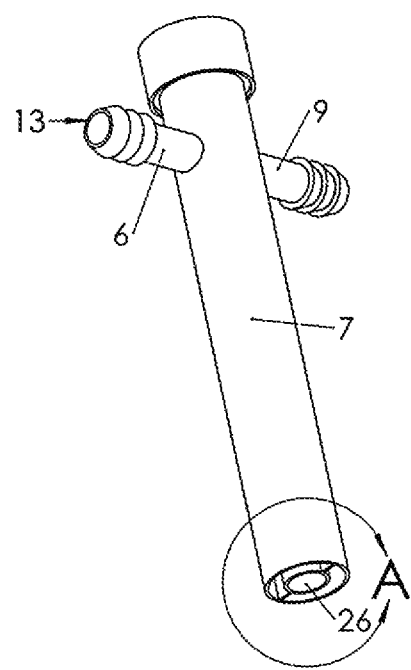
FIG. 3 is an isometric bottom view of the present invention.

FIG. 3 shows the water supply tube 6 of the cannula device Z which is an inlet port to provide saline water; the cannula sleeve of the main body 7 which is the external part of the cannula in contact with the environment; the suction port tube 9 which is an outlet port to remove waste material; the water supply port inner diameter 13 which is the internal diameter in contact with fluids; and an internal passage of cannula 26 which is a passage to introduce the surgical equipment.

Figure 4:
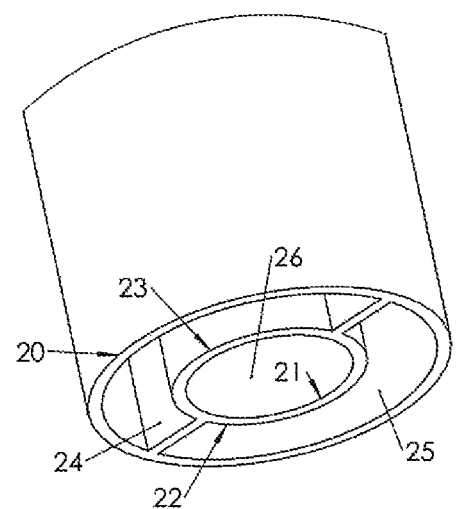
FIG. 4 is a detailed isometric bottom view of the present invention.

FIG. 4 shows a cannula outer diameter sleeve 20 for the cannula device Z which is an external diameter at the bottom open end of the cannula device Z; a passage inner diameter 21 which is an internal intermediated space to be used to place surgical equipment; a passage outer diameter A 22 which is an external intermediated space passage for fluids; a passage outer diameter B 23 which is an external intermediated space passage for waste material; a supply wall channel 24 which allows water flow through the cannula; a suction wall channel 25 which allows water suction through the cannula; and the internal passage of cannula 26 which is the passage to introduce the surgical equipment.

Figure 5:
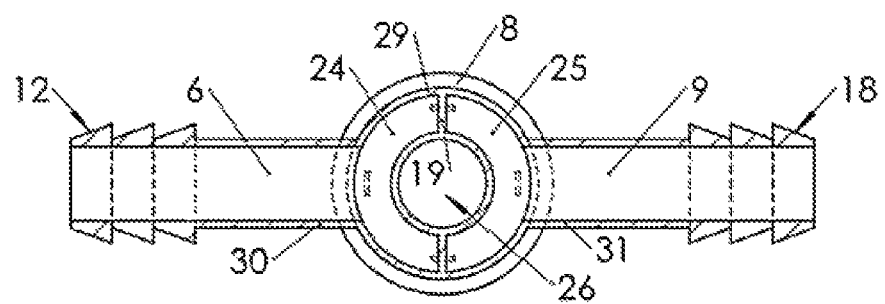
FIG. 5 is a detailed bottom view of the present invention.

FIG. 5 shows the water supply tube 6 of the cannula device Z which is an inlet port to provide saline water; the cannula cap 8 which is the thickness that provides support to the cap; the suction port tube 9 which is an outlet port to remove waste material; the water supply port total outer grip 12 which is an external threaded surface; the suction port total outer diameter grip 18 which is an external threaded surface; the supply wall channel 24 which allows water flow through the cannula; the suction wall channel 25 which allows water suction through the cannula; the internal passage of cannula 26 which is the passage to introduce the surgical equipment; a cannula thick exterior wall 29 which describes the thickness of the cannula within section; a water supply port tube thick 30 which provides support to the cannula; and a water suction port tube thick 31 which provides support to the cannula device Z.

Figure 6:
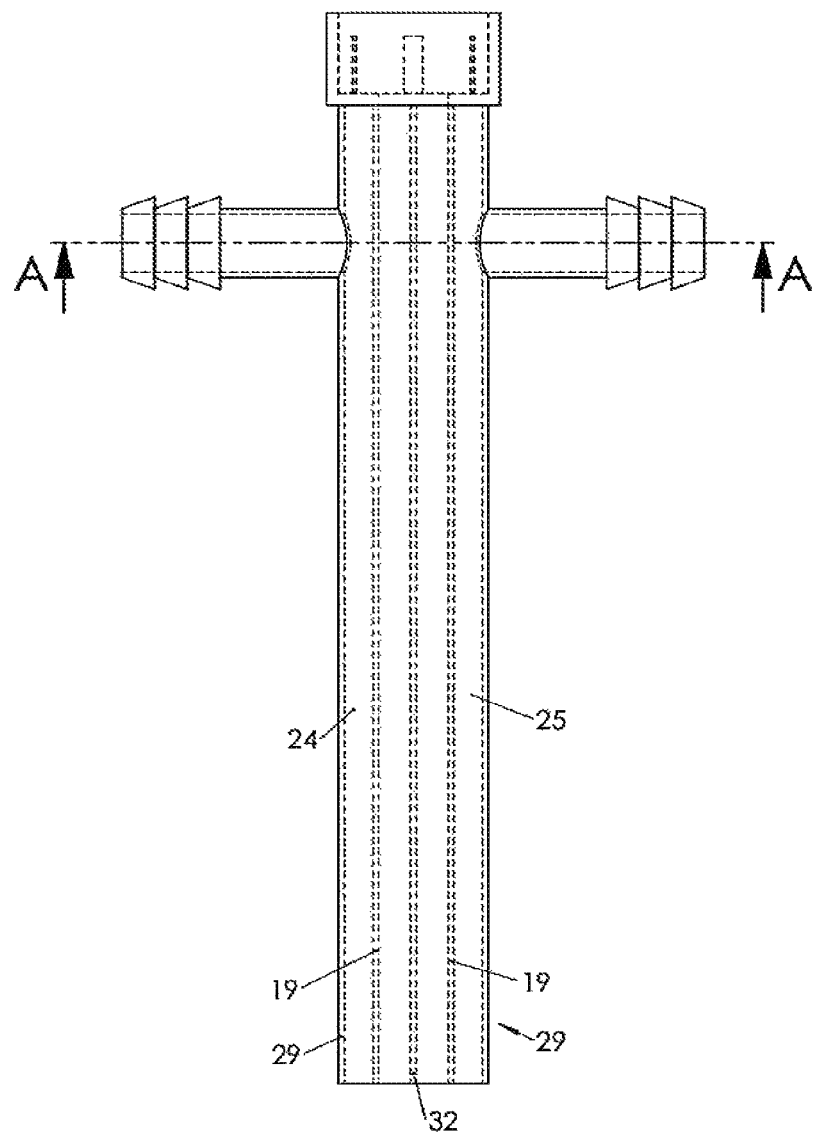
FIG. 6 is a front view of side A of the present invention.

FIG. 6 shows a separation wall 19 of the cannula device Z which is the thickness wall that divides external intermediated space passage (supply channel) for saline water from external intermediated space passage (suction channel) for waste; the supply wall channel 24 which al lows water flow through the cannula; the suction wall channel 25 which allows water suction through the cannula; the cannula thick exterior wall 29 which describes the thickness of the cannula within section; and a wall thickness 32 which is the division between ports and surgical instruments passage.

Figure 7:
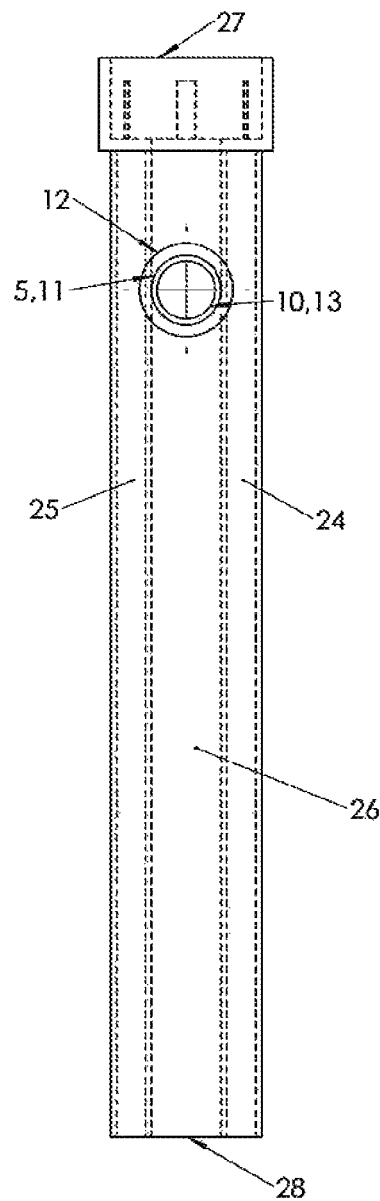
FIG. 7 is a front view of side B of the present inventions.

FIG. 7 shows the water supply port outer diameter 5 for the cannula device Z which is the external diameter in contact with the environment; the suction port inner diameter 10 which is the internal diameter in contact with waste material; the suction port inner diameter 11 which is the external diameter in contact with waste material; the water supply port total outer grip 12 which is an external threaded surface; the water supply port inner diameter 13 which is the internal diameters in contact with fluids; the supply wall channel 24 which allows water flow through the cannula; the suction wall channel 25 which allows water suction through the cannula; an internal passage of cannula 26 which is the passage to introduce the surgical equipment; the top open end of cannula 27 which is used to introduce the surgical equipment; and a bottom open end of the cannula 28 which is an external diameter at the bottom of the cannula in contact with the environment.

What is claimed is:

1. A cannula device, comprising:
    a main body having a top open end, a bottom open end and a hollow interior that is capable of receiving fluids;
    a cap seal that is removably attached to the top open end;
    a top membrane located in the hollow interior of the main body for preventing the backflow of water;
    a bottom membrane located in the hollow interior of the main body for preventing the backflow of water, wherein said bottom membrane is below the top membrane;
    a membrane base comprising holders within the hollow inner portion of the main body that provide structural support to the top membrane and the bottom membrane;
    a water supply tube transversally connected to the main body that includes an inlet port for receiving saline water;
    a suction port tube transversally connected to the main body that includes an outlet port to remove waste material; and
    a cannula cap surrounding the top open end of the main body which provides structural support to the cap seal, wherein said cannula cap is thicker than the main body.

2. The cannula device of claim 1, wherein the water supply tube comprises a water supply port whose external diameter is in contact with the environment.

3. The cannula device of claim 2, wherein the water supply port has an external threaded surface.

4. The cannula device of claim 1, wherein the suction port tube comprises an inner diameter that is in contact with waste material and an outer diameter that is in contact with the environment.

5. The cannula device of claim 4, wherein the suction port tube has an external threaded surface.

6. The cannula device of claim 1, wherein the hollow interior of the main body further comprises one or more passages capable of receiving fluids.

7. The cannula device of claim 6, wherein the one or more passages are independent of each other, separated by walls.

\* \* \* \* \*